United States Patent [19]
Heywang-Koebrunner

[11] Patent Number: 6,110,112
[45] Date of Patent: Aug. 29, 2000

[54] MEDICAL GUIDE APPARATUS FOR BREATH-COORDINATED PUNCTURING OF THE BODY OR A BODY CAVITY

[75] Inventor: Sylvia Heywang-Koebrunner, Engelsdorf, Germany

[73] Assignee: Siemens Aktiengesellschaft, Munich, Germany

[21] Appl. No.: 09/263,993

[22] Filed: Mar. 8, 1999

[30] Foreign Application Priority Data

Mar. 6, 1998 [DE] Germany .......................... 198 094 60

[51] Int. Cl.⁷ .................................................... A61B 8/00
[52] U.S. Cl. ............................................. 600/439; 600/461
[58] Field of Search ........................... 600/407, 409–410, 600/414, 415, 425, 427, 437, 439, 461, 567; 128/915; 378/37

[56] References Cited

U.S. PATENT DOCUMENTS

| | | |
|---|---|---|
| 5,053,042 | 10/1991 | Bidwell . |
| 5,280,427 | 1/1994 | Magnusson et al. ................. 600/407 |
| 5,590,655 | 1/1997 | Hussman .............................. 600/426 |
| 5,647,373 | 7/1997 | Paltieli . |
| 5,776,062 | 7/1998 | Nields ................................... 600/429 |
| 5,820,552 | 10/1998 | Crosby et al. ........................ 600/407 |

FOREIGN PATENT DOCUMENTS 29 36 259  3/1981  Germany .

*Primary Examiner*—Francis J. Jaworski
*Attorney, Agent, or Firm*—Hill & Simpson

[57] ABSTRACT

A medical guide apparatus for breath-coordinated puncturing has a puncturing instrument that is connected with an ultrasound applicator. The puncturing instrument and the ultrasound applicator are connected with a carriage that can be moved in the longitudinal direction of a patient table.

10 Claims, 3 Drawing Sheets

MEDICAL GUIDE APPARATUS FOR BREATH-COORDINATED PUNCTURING OF THE BODY OR A BODY CAVITY

BACKGROUND OF THE INVENTION

1. Field of the Invention

The present invention relates to a medical guide apparatus for breathcoordinated puncturing of the body or a body cavity, with a puncturing instrument connected to an ultrasound applicator.

2. Description of the Prior Art

A medical guide apparatus of the above type is known from U.S. Pat. No. 5,647,373. The guide apparatus enables the puncturing of sites or lesions which are visible in the ultrasound image. An ultrasound applicator and a puncturing instrument are fastened in freely movable fashion to a movable vertical support by means of a rod assembly. The rod assembly has arms that are connected movably with one another via joints. Position sensors acquire the position of the ultrasound applicator and of the puncturing instrument. The ultrasound applicator emits signals identifying the puncture target area to a control computer, and the control computer sets the direction of a puncture path to the target area. During application, the physician places the applicator on the patient for the graphic representation of the target area, and also places the point of the puncture needle on the skin surface in the vicinity of the target area. The direction of the needle is then automatically set by the guide apparatus. The puncturing can then be controlled in real time by means of simultaneously produced ultrasound tomograms. With this guide apparatus, only lesions that can be sonographically represented can be punctured. This guide apparatus is not suitable for lesions that can be made visible only by means of magnetic resonance tomography or computed tomography.

A further guide apparatus is known from German OS 29 36 259, wherein an ultrasound applicator is described to which a guide aid for a puncture instrument is fastened laterally. The guide aid is oriented in such a way that the puncture path through a body part to be examined is located in the window of the ultrasound applicator.

Puncturing aids for CT-controlled puncturings are commercially available, for example from the company Partner-Diagnostica. As a rule, these puncturing aids include a mount, a running rail graduated in centimeters, and a carriage located thereon that can be stopped. The carriage is provided with an angular scale with a mount and a pivot mechanism on which a diode laser with cross-optics is attached. Using the mount, a fixed mounting is possible for standard computed tomography systems. After determination of the puncture point and of the angle of puncture, the corresponding angle is set on the angular scale and the carriage is displaced far enough so that the laser cross coincides. This puncturing aid makes it possible to angle the puncture needle in a manner corresponding to the tilt of the CT gantry. Further angular positioning can take place within the slice plane. With such a puncture aid, a CT-controlled puncturing can be conducted on organs that are not moving. The system cannot be used if the area of examination is displaced, such as by breathing.

A puncture aid for CT-controlled puncturings is also described in U.S. Pat. No. 5,053,042. A planar guide and measurement apparatus is used in order to guide a puncture or biopsy needle to a previously determined target area specified by angular and radius coordinates in tomograms that were produced with the aid of CT exposures of the patient. The apparatus is fashioned in such a way that it can surround the body of a patient positioned on a patient table. The guide apparatus itself glides on rails that are attached to the longitudinal sides of the patient table, so that it can be positioned at any point in the longitudinal direction of the patient.

If it is necessary to puncture a site or lesion visible only in a magnetic resonance tomogram (MRT) or computed tomogram (CT), then the following problems arise due to the breath displacement of the organ. The intervention planning and the intervention are not possible in the same breath position; as a rule, the patient is not able to reproduce the breath position during the intervention planning and the intervention; and external skin markers cannot be used with organs that are displaceable by breathing. This set of problems occurs in particular for liver sites which are visible only in the magnetic resonance tomogram, but the problem is also known from computed tomography, and in that context also concerns liver sites, which for this reason are punctured—if at all possible—under sonographic control. In addition, this problem occurs in computed tomography of the lungs, where, due to the high degree of breathing movement of the caudal lung segments, lung sites are known to be difficult to puncture, especially if they are smaller than 1 cm. In comparison to computed tomography, in magnetic resonance tomography, with a closed magnetic resonance tomography apparatus, there is also the particular problem that punctures can in principle take place only outside the magnetic resonance apparatus. In addition, many puncture apparatuses are not compatible with magnetic resonance apparatuses, and thus cannot be brought into the imaging volume of the magnetic resonance apparatus.

SUMMARY OF THE INVENTION

An object of the present invention is to provide a medical guide apparatus that enables a breath-coordinated puncturing of a site which is not visible in an ultrasound tomogram, but still using ultrasound tomographic imaging.

The object is achieved in a medical guide apparatus wherein the puncture instrument and the ultrasound applicator are connected with a carriage that can be moved in the longitudinal direction of a patient table, and an arrangement for setting the puncture instrument at a target which is not individually representable with ultrasound (in contrast to a tissue reference point that can be individually represented with ultrasound) is connected with the puncture instrument. As used herein "individually representable" in the ultrasound image means a tissue structure or component which can be separately recognized apart from its surroundings in the ultrasound image. It is thereby possible to set coordinate differences between the target area which are visible only in the MR or CT image and a tissue reference point which is visible in the ultrasound image, the reference point also being visible in the MR or CT image. For the puncturing itself, a body-internal mark (tissue reference point) is used whose position changes due to breath displacement precisely as does the position of the site to be punctured. From the position of the tomograms relative to one another that contain the image of internal mark and the site to be punctured, the position of the site relative to the internal mark is determined. After the corresponding coordinates have been set on the puncture instrument, using the movable carriage the ultrasound applicator is displaced so that the internal mark moved by breathing is visible in the ultrasound tomogram. Because of the fixed allocation of the puncture instrument with the ultrasound applicator, a precise puncture of the seat is then possible.

The coordinate difference between the tissue reference point and the target area can be set and fixed on the basis of a CT or MR image data set of the overall examination volume, either in computer-controlled fashion or manually.

DESCRIPTION OF THE PREFERRED EMBODIMENTS

Figure 1:
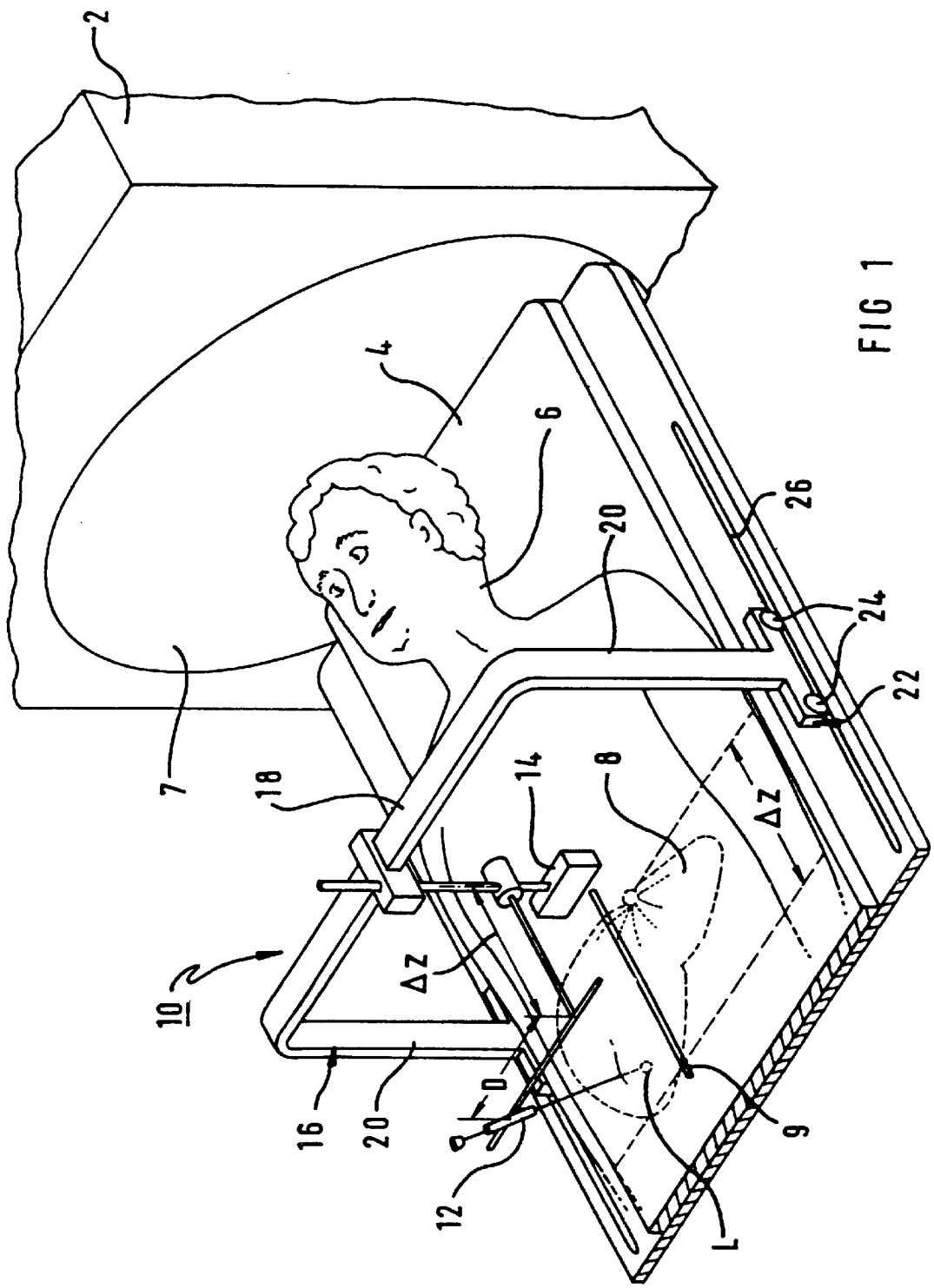
FIG. 1 shows a perspective view of a medical guide apparatus for breath-coordinated puncturing, in accordance with the invention.

FIG. 1 shows a section of a magnetic resonance tomography apparatus 2, designated MRT apparatus in the following, with a patient table 4 on which a patient 6 to be examined is positioned. By means of the patient table 4, the patient 6 can be moved into a cylindrical examination chamber or an examination tube 7 of the MRT apparatus 2, in order to produce magnetic resonance tomograms of an area of examination 8, here the liver, in which a site or a lesion L is suspected. Parallel to the body axis, a small tube 9, filled with a contrast agent, is fastened to the patient 6, for example by means of plastic strips. The contrast agent produces visible marks in all magnetic resonance tomograms produced by the examination area. These marks are used for the setting and orientation of a guide apparatus 10, as is further described below.

The guide apparatus 10 is arranged so as to be movable in the longitudinal direction on the patient table 4. The guide apparatus 10 includes a puncture instrument 12 and an ultrasound applicator 14 that are connected with a carriage 16. The carriage 16 is U-shaped, with a base segment 18 and arms 20 connected laterally thereto. At the ends of both arms 20, a system of rollers 22 is arranged with pivotably mounted rollers 24. The rollers 24 run in grooves or slots 26 that are formed in the longitudinal direction on both longitudinal sides of the patient table 4. The grooves 26 are fashioned long enough so that the guide apparatus 10 can be displaced in a manner corresponding to a maximum possible breath displacement of the organs to be examined. The overall guide apparatus 10 is easily placed on the patient table and also easily removed. As an alternative to the roller system 22, other displacement mechanisms, such as carriage rails guided in grooves, can be used. Carriage rails have the advantage that no moving parts are used.

Figure 2:
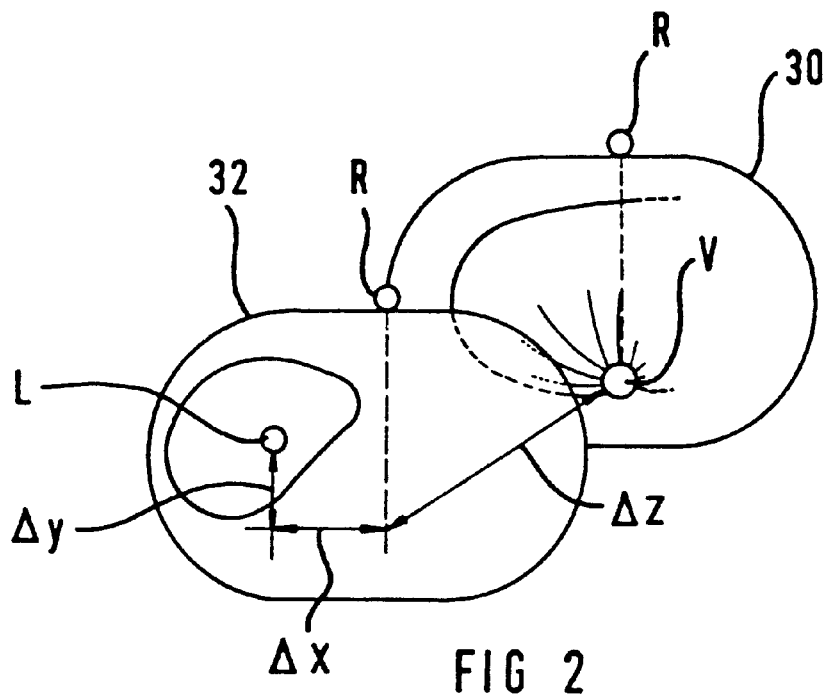
FIG. 2 shows two magnetic resonance tomograms from which the relative position of a seat in reference to a body-internal mark can be determined, in accordance with the invention.
Figure 3:
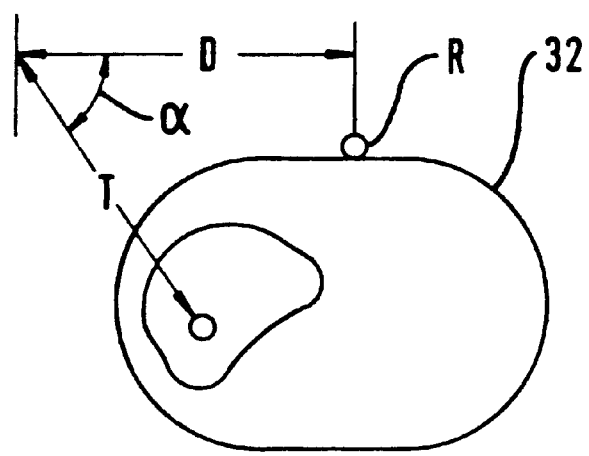
FIG. 3 shows a tomogram containing an image of the site to be punctured, in order to determine an insertion angle and an insertion depth for the puncturing in accordance with the invention.

FIG. 2 shows a first tomogram 30 from a volume scanning of the examination area by means of magnetic resonance, in which a body-internal mark or an internal reference V is visible. If the examination region 8 represents the liver, then the venous star, for example, can be used as the internal reference V; however, the upper or lower edge of the liver is also possible as a freely selectable reference point. In addition, FIG. 2 shows a second tomogram 32 from the volume scanning, in which a site to be punctured or a lesion L to be punctured is visible. As mentioned above, the small tube 9 is oriented toward the skin surface in the direction of the body's longitudinal axis (e.g., direction of an xyz coordinate system), which proceeds parallel to the axis of the examination tube 7. The position transverse to the body longitudinal axis, i.e. in the direction of the x axis of the xyz coordinate system, is chosen in such a way, by a first orienting ultrasound examination, that it is arranged directly over the internal reference point V on the skin surface. From the two tomograms 30 and 32, it is now possible to determine the coordinates of the lesion L with reference to the internal reference V. A coordinate value $\Delta z$ results from the distance of the two tomograms 30 and 32 to one another. The coordinate value $\Delta x$ is determined in the lesion tomogram 32 from imagings R of the small tube 9 in the two tomograms 30 and 32. Finally, the coordinate value $\Delta y$ can be determined in the lesion tomogram 32.

As in any CT-supported or MRT-supported planning, a transverse displacement D and a penetration depth T can be measured in the lesion layer 32 from the coordinates of the lesion L and from a puncture angle a that can be freely selected from the anatomical points of view. This is achieved for example with standard magnetic resonance apparatus software, whereby a precise later position of the ultrasound applicator 14 on the skin is identified by the small tube 9 proceeding parallel to the body axis.

Figure 4:
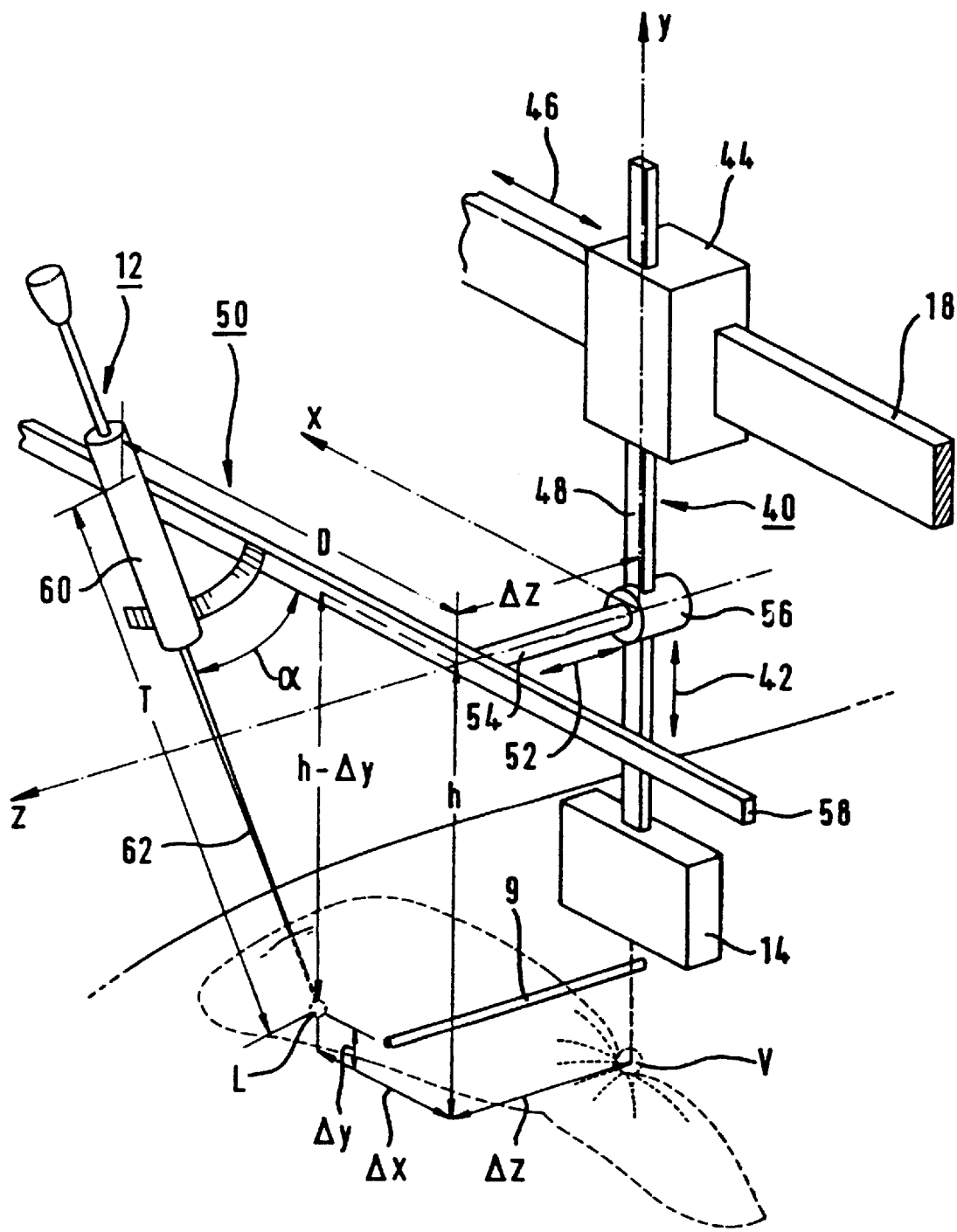
FIG. 4 shows the puncture instrument in detail, with the ultrasound applicator according to FIG. 1.

The positioning possibilities of the puncture instrument 12 will now be explained on the basis of FIG. 4. By means of a first rod assembly 40, the ultrasound applicator 14 is connected movably with the carriage. The movability is symbolized by a double arrow 42, and defines the y-coordinate of an xyz coordinate system. For this purpose, the first rod assembly 40 has a first connecting element 44, which is connected with the base segment 18 movably (double arrow) and so as to be capable of being locked. The movability on the base segment 18 also defines the x-coordinate of the xyz coordinate system. In the first connecting element 44, a first rod-shaped element 48, to which the ultrasound applicator 14 is fastened, is arranged in movable and lockable fashion. For clarity, the fixing means, e.g. in the form of fastening screws or bolts, is not shown.

By means of a second rod assembly 50, the puncturing instrument 12 is connected movably, so as to be able to be locked in relation to the ultrasound applicator 14. The movability is symbolized by a double arrow 52, which simultaneously defines the z-direction of the xyz coordinate system. For this purpose, the second rod assembly 50 has a second rod-shaped element 54, which is arranged in a second connection element 56 so as to be able to be moved and to be locked. On the second rod-shaped element 54, a third rod-shaped element 58 is fastened parallel to the x-coordinate direction, to which the puncturing instrument 12 is fastened in movable, pivotable, and lockable fashion. As for the first rod assembly 40, in the second rod assembly 50 as well the above-mentioned locking elements are not shown clarity. The puncturing instrument 12 can be equipped with a mount 60 for a needle 62 or for a biopsy pistol or the like, however, it can alternatively contain only a laser pointer that allows a free needle guiding. A light mark then shows the insertion point on the skin surface. The correct orientation of the needle 62 is then indicated when the laser beam strikes the rear end of the needle 62 in the center.

For the preparation of the puncturing, first the relative coordinates $\Delta z$, D and the angle a of the lesion L in relation to the reference point V are fixedly set. Already during these settings, the patient, given an otherwise unchanged position, can be moved out of the magnetic resonance tomography apparatus or the computed tomography apparatus, under the guide apparatus 10. At this point the patient must again hold his breath. During the holding of the breath, the entire guide apparatus is moved until the ultrasound head is located precisely over the reference point V and the reference point is imaged in real time in the ultrasound image. The puncturing can now take place by moving the needle, already correctly positioned via the rod assembly 40 and 50, by the puncture depth T.

Although modifications and changes may be suggested by those skilled in the art, it is the intention of the inventor to embody within the patent warranted hereon all changes and modifications as reasonably and properly come within the scope of her contribution to the art.

I claim as my invention:

1. A medical guide apparatus for use with a patient table, comprising:

a puncturing instrument;

an ultrasound imaging system including an ultrasound applicator, said ultrasound imaging system producing an ultrasound image of a body region including a tissue reference point visible in said ultrasound image;

a carriage adapted for longitudinal movement relative to said patient table; and a manually adjustable mounting structure attaching said puncturing instrument and said ultrasound applicator to said carriage comprising a rod assembly movably connecting said ultrasound applicator to said carriage allowing manipulation of said puncturing instrument to set said puncturing instrument relative to said tissue reference point to puncture a site in said body which is not individually represented in said ultrasound image.

2. A medical guide apparatus as claimed in claim 1 wherein said carriage comprises rollers adapted to roll in grooves disposed along longitudinal sides of said patient table.

3. A medical guide apparatus as claimed in claim 1 wherein said carriage has a U-shape with a base and two arms connected to said base, each of said arms having a free end which is adapted for movable engagement with said patient table.

4. A medical guide apparatus as claimed in claim 1 wherein said first rod assembly includes a locking element for locking said ultrasound applicator in a locked position relative to said carriage after adjusting a position of said ultrasound applicator relative to said carriage.

5. A medical guide apparatus as claimed in claim 1 wherein said rod assembly is a first rod assembly, and wherein said mounting structure comprises a second rod assembly movably connecting said puncturing instrument to said carriage and allowing movement of said puncturing instrument relative to said carriage and relative to said ultrasound applicator.

6. A medical guide apparatus as claimed in claim 1 wherein said carriage has U-shape with a base segment and two arms attached to said base segment, and wherein said rod assembly comprises a connecting element movably unlockably connected to said base segment and a rod element movably and lockably received in said connecting element, said ultrasound applicator being fastened to said rod element.

7. A medical guide apparatus as claimed in claim 6 wherein said rod assembly is a first rod assembly and said connecting element comprises a first connecting element, and wherein said mounting structure further comprises a second rod assembly movably and lockably connected to said carriage, on which said puncturing instrument is attached, said second rod assembly comprising a second connecting element movably and lockably connected to said rod element.

8. A medical guide apparatus as claimed in claim 7 wherein said rod element is a first rod element, and wherein said second rod assembly comprises a second rod element movably and lockably received in said second connecting element.

9. A medical guide apparatus as claimed in claim 8 wherein said second rod assembly comprises a third rod element disposed perpendicularly to said second rod element.

10. A medical guide apparatus as claimed in claim 9 wherein said puncturing instrument comprises a needle guide which is pivotably and lockably attached to said third rod element.

* * * * *